(12) United States Patent
Nelson (10) Patent No.: US 8,784,349 B1
(45) Date of Patent: Jul. 22, 2014

(54) KNEE BRACE

(75) Inventor: Ronald E. Nelson, Cambridge, MN (US)

(73) Assignee: Mueller Sports Medicine, Inc., Prairie du Sac, WI (US)

( * ) Notice: Subject to any disclaimer, the term of this patent is extended or adjusted under 35 U.S.C. 154(b) by 55 days.

(21) Appl. No.: 13/303,505

(22) Filed: Nov. 23, 2011

(51) Int. Cl.
*A61F 5/00* (2006.01)

(52) U.S. Cl.
USPC .................. 602/26; 602/23; 602/60; 602/61; 602/62

(58) Field of Classification Search
USPC .......................................... 602/23, 26, 60–62
See application file for complete search history.

(56) References Cited

U.S. PATENT DOCUMENTS

| | | |
|---|---|---|
| 4,366,813 A | 1/1983 | Nelson |
| 4,726,362 A | 2/1988 | Nelson |
| D573,713 S | 7/2008 | Mueller et al. |
| D580,554 S | 11/2008 | Lin et al. |
| D580,556 S | 11/2008 | Lin et al. |
| 7,615,019 B2 * | 11/2009 | Nordt et al. ....................... 602/5 |
| 2003/0204156 A1 | 10/2003 | Nelson |
| 2004/0176715 A1 | 9/2004 | Nelson |
| 2004/0225245 A1 | 11/2004 | Nelson |
| 2007/0106191 A1 | 5/2007 | Mueller et al. |

* cited by examiner

*Primary Examiner* — Patricia Bianco
*Assistant Examiner* — Keri J Nelson
(74) *Attorney, Agent, or Firm* — Rick L. Abegglen (57) ABSTRACT

A knee brace for use by athletes or others requiring protection and support of the knee. The knee brace protects against abnormal motions of the knee, and provides direct and indirect patella stabilization. A base comprised of elastic material is configured to closely fit around portions of the knee and adjacent leg portions. The knee brace includes at least one upright support member attached to a lateral side of the base, where the upright support member is curved with an upper portion bending away from the front central axis of the brace and a lower portion that bends toward the front central axis of the brace.

20 Claims, 7 Drawing Sheets

KNEE BRACE

FIELD OF THE INVENTION

This invention relates generally to the field of articles worn by persons to reduce the likelihood, severity, or exacerbation of injury to the body, and more specifically to the field of braces worn on the knee.

BACKGROUND OF THE INVENTION

Flexible knee braces are used by athletes and other persons engaged in vigorous physical activity to protect the knee from injury and to avoid exacerbation of existing injury. The knee is one of the most heavily used joints of the body, as it is used in any activity that involves walking or running. The knee is also a common subject of injury, due to the relatively high levels of stress it must bear. During normal ambulation, in occupations involving physical labor, and especially during strenuous sports, the knee can undergo abnormal motions as a result of quick changes in direction, fatigue, uneven surfaces, or impacts. These abnormal motions can cause sprains or more serious injuries, including dislocation, stretching, or tearing of the tissues that make up the knee.

Devices to protect the knee against abnormal motions have been used for many years, in a variety of specific embodiments which vary in their abilities to protect against the different types of abnormal motions. Besides protecting the knee against abnormal motions, the devices sometimes provide additional benefits such as insulating the knee to keep it warm, protecting the knee against impact, or compressing the knee to reduce discomfort. However, prior art devices may incur a reduction in range or ease of normal motion, or may have other undesirable aspects such as added weight on the leg, potential for self-injury or injury to others caused by rigid components, difficulty of application and removal, cost, appearance, and irritation or chafing of the skin.

For these reasons, there has long been motivation to find a knee brace which offers improved protection from abnormal motions without affecting the range or ease of normal motion, while avoiding the undesirable aspects of prior art devices.

SUMMARY OF THE INVENTION

A knee brace according to the present invention includes a base with lateral sides, an upper end, and a lower end, wherein the knee brace has a front central axis when the knee brace is worn. The brace includes at least one upright support member comprising a resilient stay and fastened to a lateral side, where the upright support member has an upper portion, a central portion, and a lower portion, and wherein the upper portion is farther from the front central axis than the central portion, and the central portion is farther from the front central axis than the lower portion.

According to another aspect of the invention, the knee brace includes a base with lateral sides, an upper end, and a lower end, wherein the knee brace has a rear central axis when the knee brace is laid flat. The brace includes at least one upright support member comprising a resilient stay and fastened to a lateral side, where the upright support member has an upper portion, a central portion, and a lower portion, and wherein the upper portion is closer to the rear central axis than the central portion, and the central portion is closer to the rear central axis than the lower portion.

According to a third aspect of the invention, the knee brace includes a base with lateral sides, an upper end, and a lower end, wherein the knee brace has a front central axis when the knee brace is worn. The brace includes at least one upright support member comprising a resilient stay and fastened to a lateral side, where the upright support member has an upper portion, a central portion, and a lower portion, and wherein the second upper portion curves away from the front central axis and the second lower portion curves toward the front central axis, whereby the second upright support member is generally shaped like the letter S.

Further objects, features, and advantages of the invention will be apparent from the following detailed description when taken in conjunction with the accompanying drawings.

DETAILED DESCRIPTION OF THE INVENTION

Referring to the drawings, FIGS. 1-4 show a preferred embodiment of a knee brace according to the invention indicated generally at 20. As normally worn by a person, the upper leg 22 extends from an opening at the upper end 40 of the knee brace 20, and the lower leg 24 extends from an opening at the lower end 48 of the knee brace 20.

Figure 4:
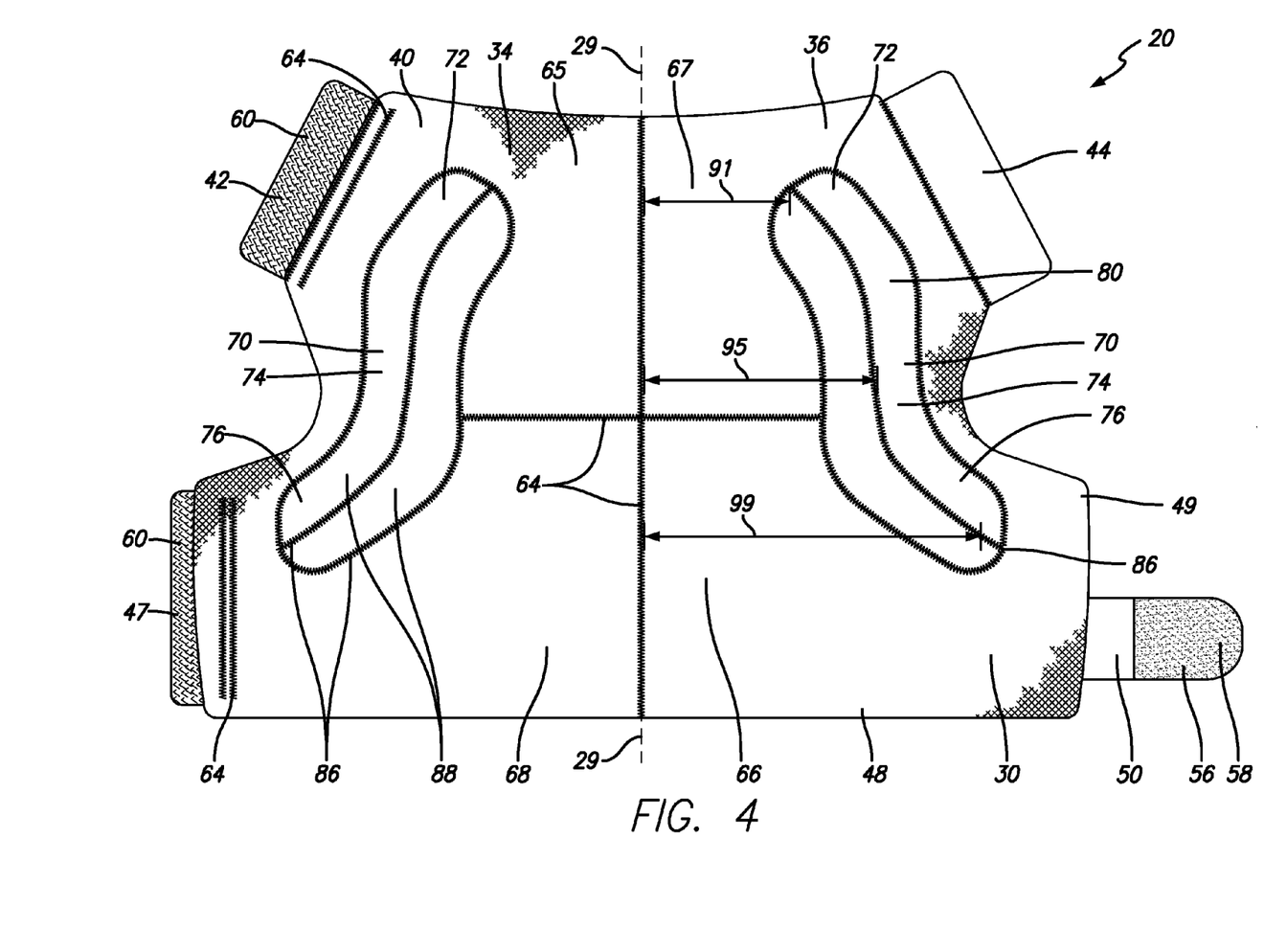
FIG. 4 is a plan view of the inside surface of a knee brace according to the invention laid flat.

The knee brace 20 includes a base 30, having a front side 32 (best shown in FIGS. 1A and 1B) that faces forward, and a rear side 38 (best shown in FIGS. 2A and 2B) that faces rearward, when the brace 20 is worn by a person. The brace 20 has a first side 34 (best shown in FIG. 2A) and a second side 36 (best shown in FIG. 2B). As shown in FIG. 4, the base 30 can be formed of two separate pieces (corresponding to first side 34 and second side 36) that are joined together along the vertical seam 64 shown in FIG. 4, with each separate piece cut to help the base conform to the knee and then sewn together along the horizontal seam 64 shown in FIG. 4. The base 30 is preferably formed as a reclosable sleeve made from a sheet of elastic material of a type that can provide generalized support and compression to the knee area, along with therapeutic warming, but other materials may be used. Alternatively, the base 30 may be formed, for example, of a tubular elastic sleeve shaped to fit snugly about the knee and adjacent leg portions.

The base 30 may include a patella opening 46 which generally matches the size of the patella, such that the patella (kneecap) 26 of the wearer extends from the patella opening 46 when the brace 20 is worn, although this is not necessary. In addition to providing direct patella stabilization during use, the patella opening 46 may help to locate the brace 20 with respect to the patella 26 during application of the brace 20.

The base 30 preferably includes an upper base fastening tab 42 bearing hook-type fastening material 60 and an upper base fastening patch 44 bearing loop-type fastening material 62. When the base 30 of the knee brace 20 is wrapped about the leg of a person, the upper base fastening tab 42 and the upper base fastening patch 44 overlap, allowing the hook-type fastening material 60 and the loop-type fastening material 62 to be pressed together to form a detachable attachment that retains the knee brace 20 on the upper leg 22.

Figure 1A:
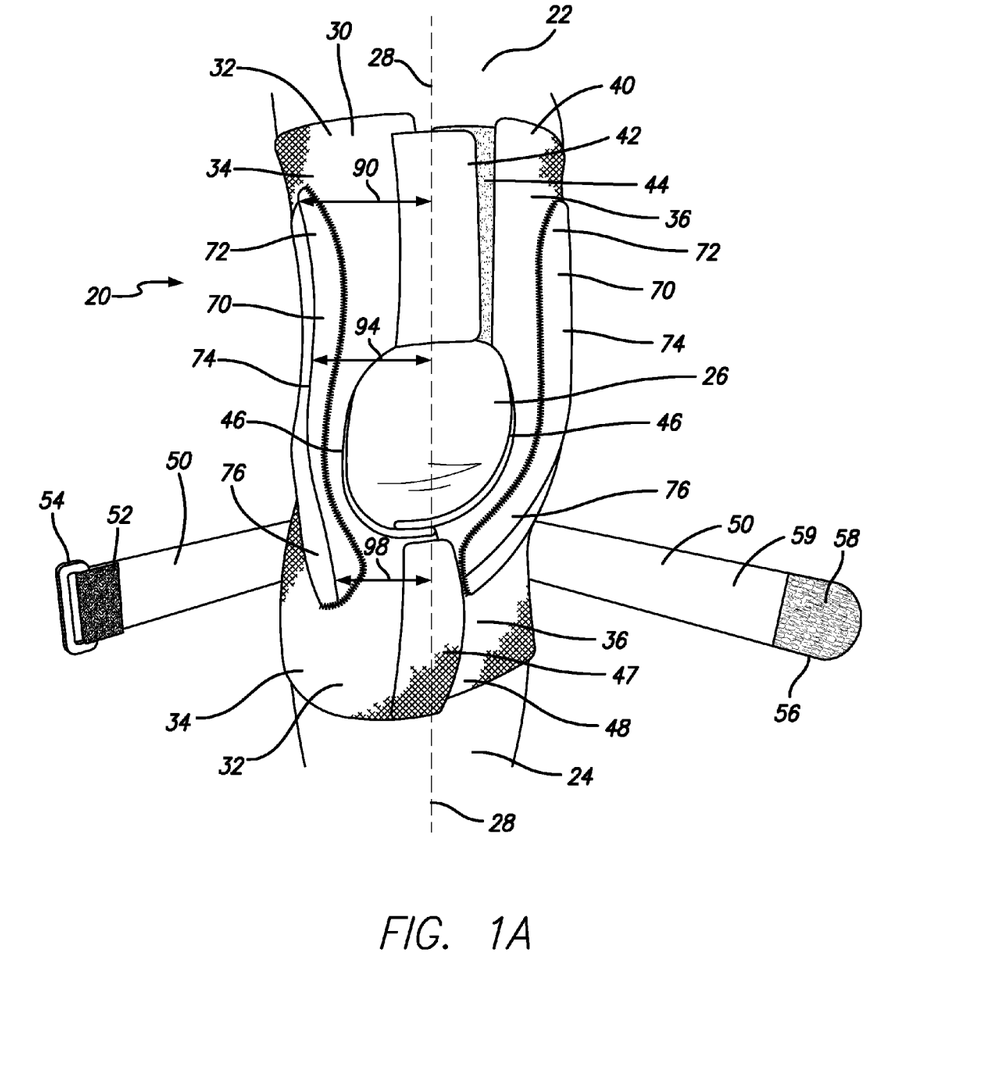
FIG. 1A is a front perspective view of a knee brace according to the invention fitted on the leg of a person, with the lower strap unfastened.
Figure 1B:
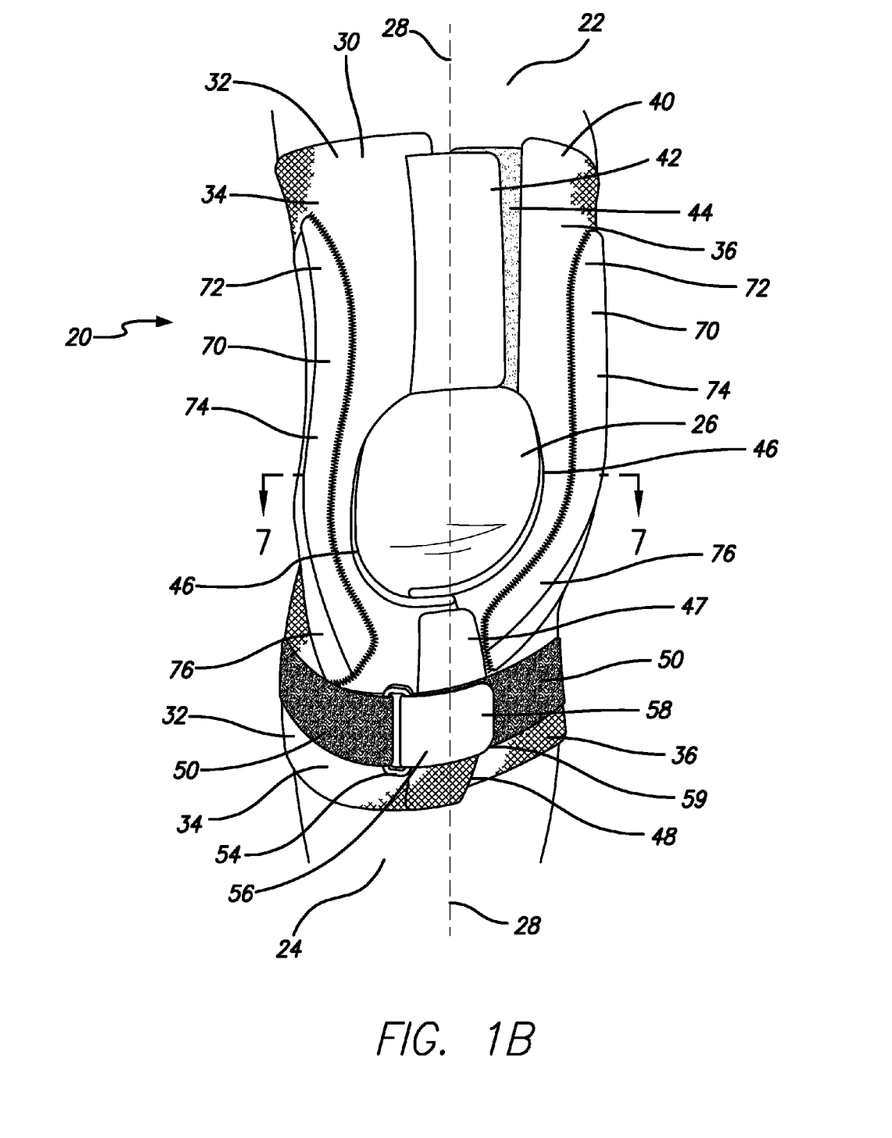
FIG. 1B is a front perspective view of a knee brace according to the invention fitted on the leg of a person, with the lower strap fastened.
Figure 2A:
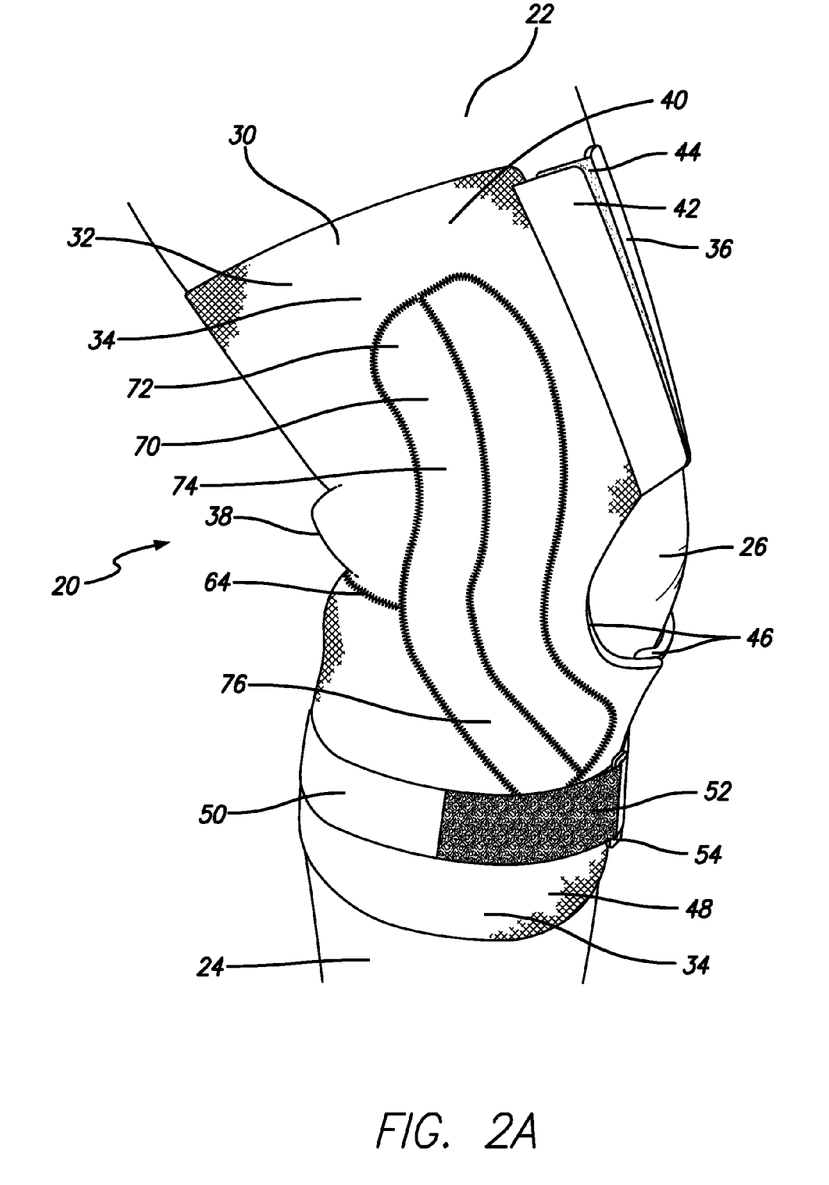
FIG. 2A is a first side view of a knee brace according to the invention fitted on the leg of a person.
Figure 2B:
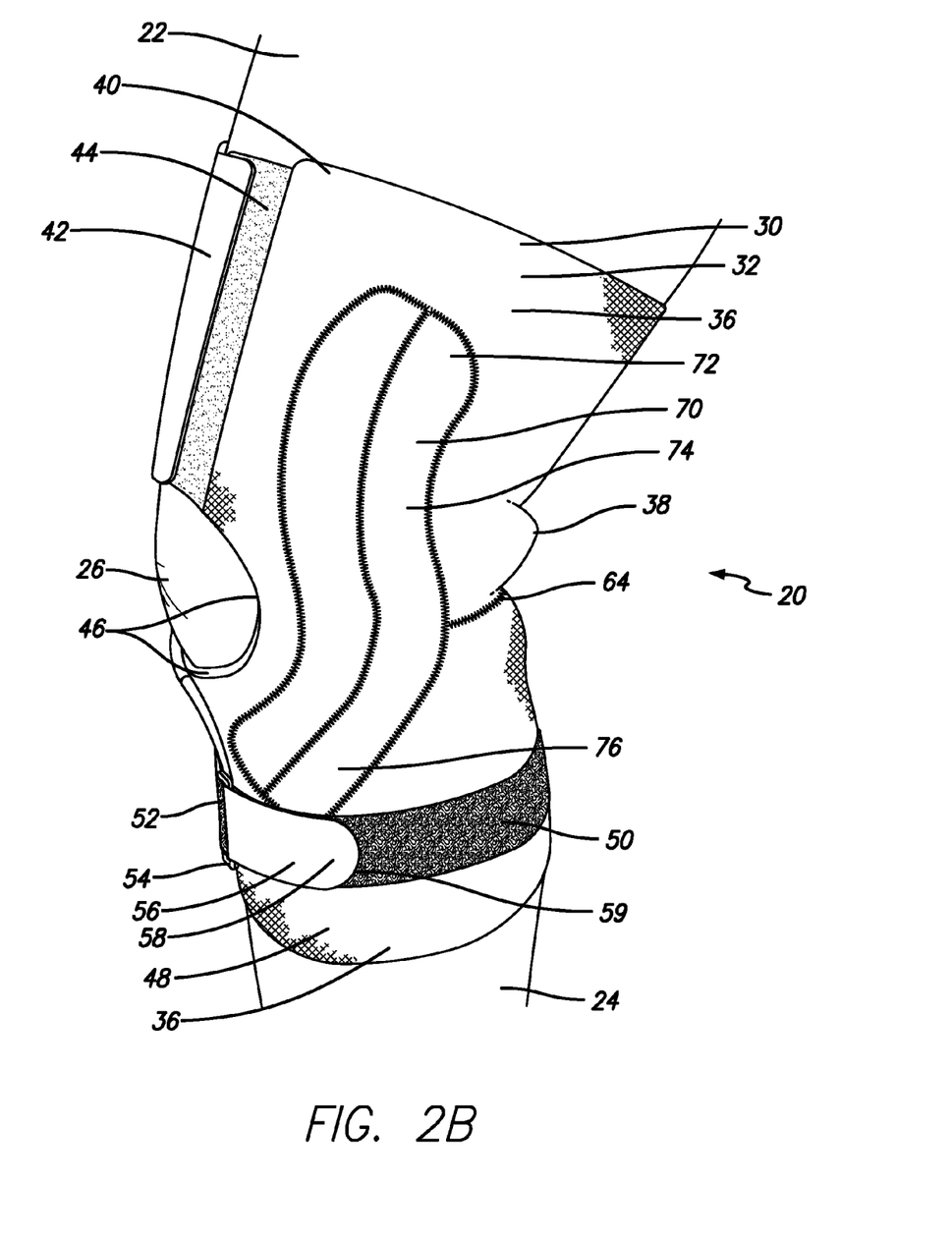
FIG. 2B is a second side view of a knee brace according to the invention fitted on the leg of a person.

Similarly, the base 30 preferably includes a lower base fastening tab 47 bearing hook-type fastening material 60 and a lower base fastening patch 49 bearing loop-type fastening material 62 to provide a detachable attachment that retains the knee brace 20 on the lower leg 24. In addition, the brace 20 preferably includes a strap 50 with a first end 52 bearing a reversing loop 54. The second end 56 of the strap 50 may have strap fastening tab 58 bearing hook-type fastening material 60 and a strap fastening patch 59 bearing loop-type fastening material 62. As shown in FIG. 1A, after passing the second end 56 through the reversing loop 54, the strap 50 can be placed under tension and then the strap fastening tab 58 can be pressed against the strap fastening patch 59 to form a detachable attachment that further retains the brace 20 on the lower leg 24.

Figure 5:
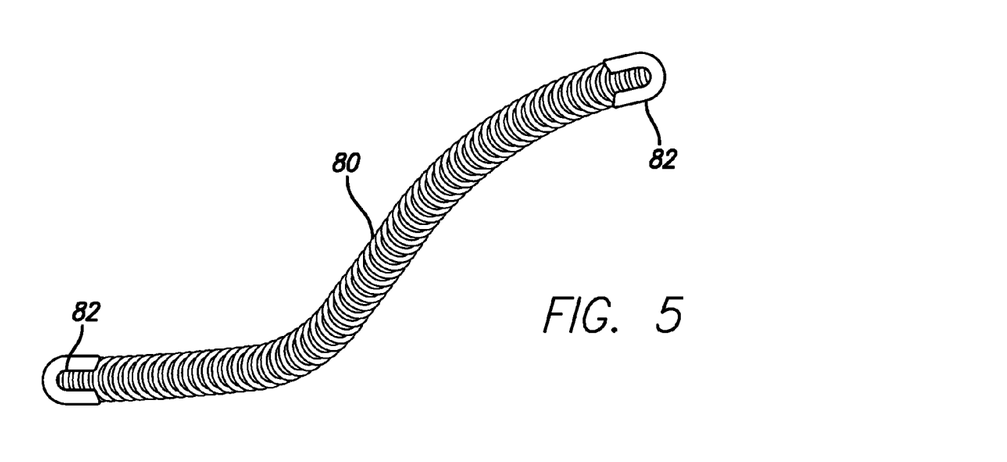
FIG. 5 is a front view of an exemplary resilient stay member.
Figure 6:
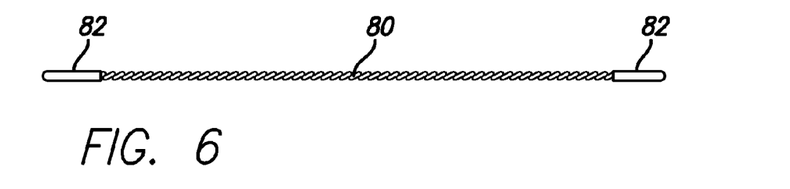
FIG. 6 is a side view of an exemplary resilient stay member.
Figure 7:
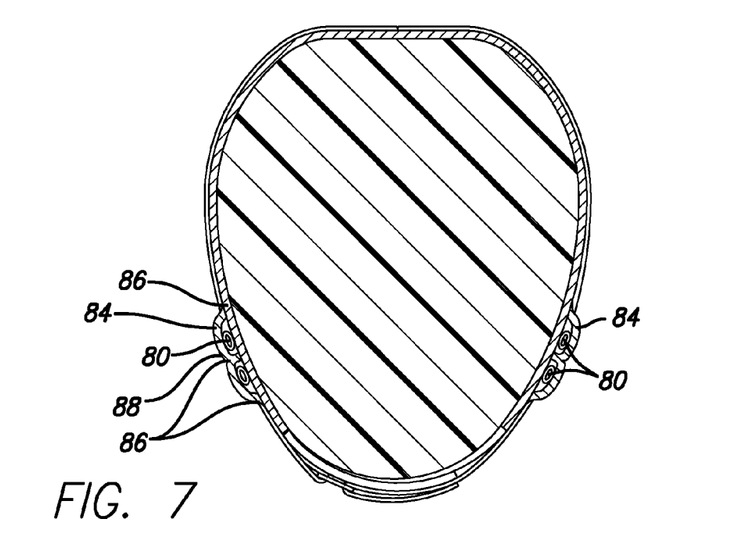
FIG. 7 is a cross-sectional view of the knee brace of FIG. 1B taken along the line 7-7 thereof.

As shown in the figures, including the cross-section in FIG. 7, one or more curved upright support members 70 are provided on the first side 34 and/or the second side 36 of the knee brace 20, to provide support and protect the knee against abnormal motions. By way of example and not as a limitation, each curved upright support member 70 may be formed by placing a curved resilient stay member 80 in an elongated side pocket 84. As shown in FIGS. 5 and 6, each resilient stay member 80 preferably comprises a flattened spiral core of stainless steel or other flexible material of conventional construction commonly used in various types of braces, bent to the required shape with end caps 82 at each end.

Each elongate side pocket 84 may be formed, for example, between stitches 86 that fix a side pocket cover strip 88 to the base 30. The side pocket cover strip 88 may be made of the same elastic sheet material as the base 30, although this is not necessary. Edge binding may be fastened to the edges of the side pocket cover strips 88, and/or to the edges of the base 30, although this is not necessary.

Importantly, and perhaps best shown in FIGS. 1A, 3, and 4, the curved upright support members 70 include a lower portion 76 below the patella, a central portion 74 alongside the patella, and an upper portion 72 above the patella when the brace 20 is worn by a person.

As shown in FIG. 1A, the lower portion 76 bends toward the front central axis 28 of the brace 20 and the upper portion 72 bends away from the front central axis 28, while the central portion 74 occupies a lateral position (relative to the front central axis 28) between the upper portion 72 and the lower portion 76. In other words, the lateral distance 90 (from the upper portion 72 to the front central axis 28) is greater than the lateral distance 94 (from the central portion 74 to the front central axis 28), and the lateral distance 94 is greater than the lateral distance 98 (from the lower portion 76 to the front central axis 28).

Figure 3:
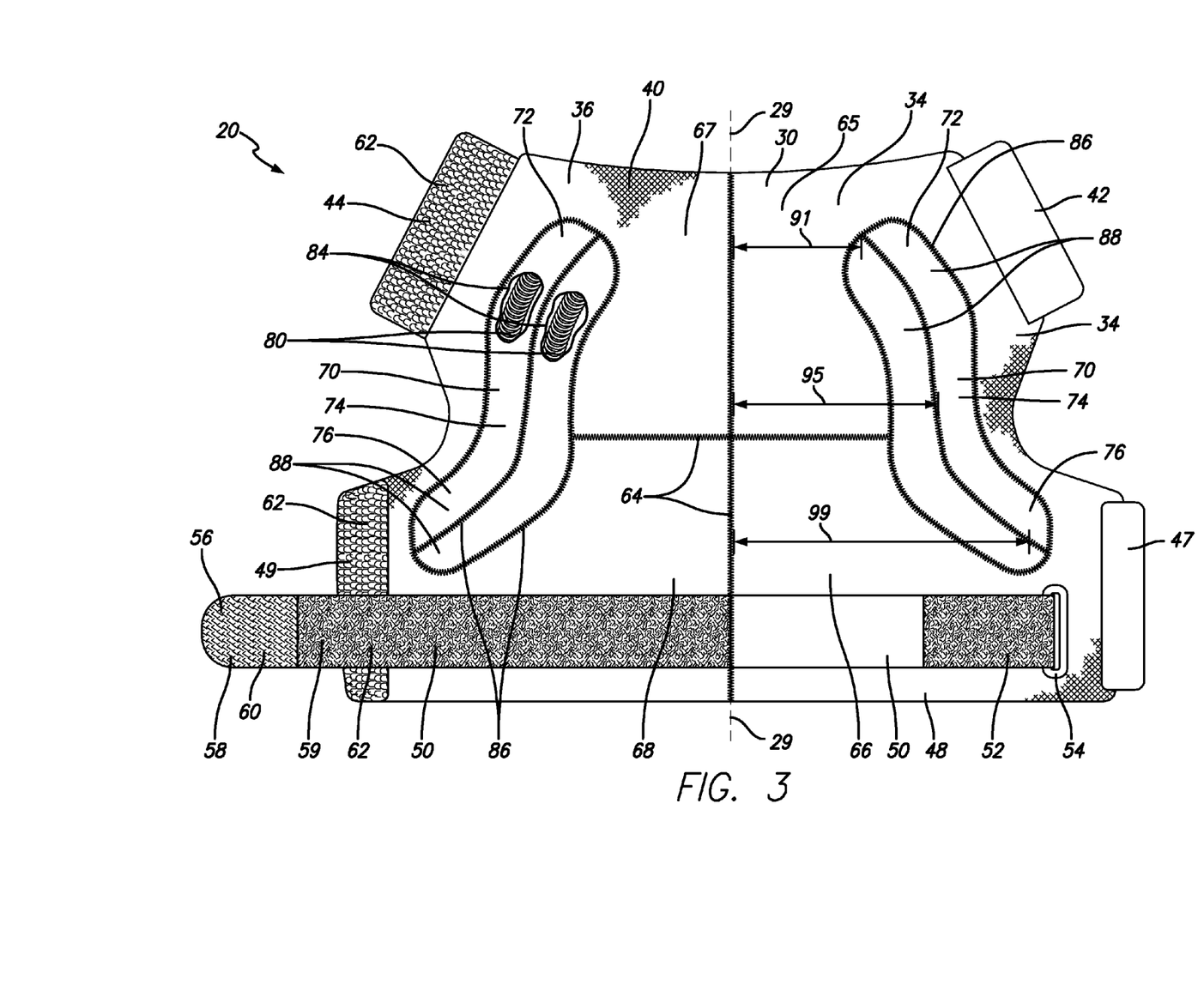
FIG. 3 is a plan view of the outside surface of a knee brace according to the invention laid flat.

As shown in FIGS. 3 and 4, with the brace 20 laid flat (the term "laid flat" meaning substantially flat notwithstanding minor contours arising from the fitted nature of the base 30), the lower portion 76 bends away from the rear central axis 29 and the upper portion 72 bends toward the rear central axis 29, while the central portion 74 occupies a lateral position (relative to the rear central axis 29) between the upper portion 72 and the lower portion 76. In other words, the lateral distance 91 (from the upper portion 72 to the rear central axis 29) is less than the lateral distance 95 (from the central portion 74 to the rear central axis 29), and the lateral distance 95 is less than the lateral distance 99 (from the lower portion 76 to the rear central axis 29).

There are various possibilities with regard to alternative embodiments of a knee brace according to the invention.

Although in a preferred embodiment the knee brace 20 includes a base 30 which is formed as a reclosable sleeve made from one or more sheets of elastic material, this is not required. For example, the base 30 may also be formed of a tubular elastic sleeve shaped to fit snugly about the knee and adjacent leg portions. The base 30 does not need to include a patella opening 46. The patella opening 46, if present, could have a variety of shapes, e.g. circular, square, rectangular, elliptical, diamond, trapezoidal, or any substantial equivalent. All such alternative embodiments will be referred to herein as a base.

Although in a preferred embodiment the base is detachably fastened about the leg of the wearer using hook and loop material of the type which adheres when pressed together, this is not required. For example, other reclosable fasteners such as buttons, clasps, buckles, pins, zippers, straps, buttons or other substantial equivalents may be substituted for the hook and loop type fastener material.

Although in a preferred embodiment, various components are permanently fastened together using stitches, this is not required. For example, other means such as glue, thermal bonding, rivets, or other permanent attachment methods or structures could be used.

Although in a preferred embodiment, two upright support members 70, each comprising two resilient stays 80, are provided on the first side 34 and second side 36 of the base 30 of the knee brace 20, this is not necessary, and the exact number, location, and construction of the upright support members 70 may vary. For example, there may be a single elongated side pocket 84 containing a single resilient stay 80 and forming only one upright support member 70, or there may be a greater number of upright support members 70 or resilient stays 80. The elongated side pockets 84 may be openable at one end to allow removal of the resilient stays 80 prior to washing the brace, or so that different resilient stays 80 may be inserted to adjust the amount and type of support provided. The resilient stays 80 may have a different construction, such as plastic, metal, or graphite rods or strips of reinforcing sheet material, or other substantial equivalents, or a combination of these various alternatives.

It is understood that the invention is not confined to the embodiments set forth herein as illustrative, but embraces all such forms thereof that come within the scope of the following claims.

What is claimed is:

1. A knee brace, comprising:
   (a) a base wearable in snug covering relationship to portions of a knee and adjacent portions of an upper leg and a lower leg of a person, the knee having a patella and the base having a first lateral side, an upper end, and a lower end;
   (b) a first upright support member fastened to the first lateral side, the first upright support member having a first upper portion, a first central portion, and a first lower portion, and wherein the first upright support member comprises at least one resilient stay;
   (c) wherein the knee brace has a front central axis when the knee brace is worn, wherein the first upper portion is at a greater lateral distance from the front central axis than the first central portion, and wherein the first central portion is at a greater lateral distance from the front central axis than the first lower portion; and (d) wherein the first lower portion extends toward the front central axis and adjacent and directly underneath at least a portion of the patella along a front surface of the lower leg, whereby the knee brace provides indirect support to the patella.

2. The knee brace of claim 1 wherein the base has a second lateral side, and further comprising (e) a second upright support member fastened to the second lateral side, the second upright support member having a second upper portion, a second central portion, and a second lower portion, and wherein the second upright support member comprises at least one resilient stay;

(f) wherein the second upper portion is at a greater lateral distance from the front central axis than the second central portion, and wherein the second central portion is at a greater lateral distance from the front central axis than the second lower portion; and (g) wherein the second lower portion extends toward the front central axis and adjacent and directly underneath at least a portion of the patella along a front surface of the lower leg, whereby the knee brace provides indirect support to the patella.

3. The knee brace of claim 1 wherein the base is a tubular sleeve.

4. The knee brace of claim 1 wherein the base is an openable and reclosable sleeve.

5. The knee brace of claim 1 wherein the base includes a patella opening.

6. The knee brace of claim 5 wherein the patella opening is roughly circular.

7. The knee brace of claim 1 wherein the resilient stay includes a flattened spiral core.

8. A knee brace, comprising:

(a) a base wearable in snug covering relationship to portions of a knee and adjacent portions of an upper leg and a lower leg of a person, the knee having a patella and the base having a first lateral side, an upper end, and a lower end;

(b) a first upright support member fastened to the first lateral side, the first upright support member having a first upper portion, a first central portion, and a first lower portion, and wherein the first upright support member comprises at least one resilient stay;

(c) wherein the knee brace has a rear central axis when the knee brace is laid flat, wherein the first upper portion is at a lesser lateral distance from the rear central axis than the first central portion, and wherein the first central portion is at a lesser lateral distance from the rear central axis than the first lower portion; and (d) wherein the first lower portion extends toward the front central axis and adjacent and directly underneath at least a portion of the patella along a front surface of the lower leg, whereby the knee brace provides indirect support to the patella.

9. The knee brace of claim 8 wherein the base has a second lateral side, and further comprising (e) a second upright support member fastened to the second lateral side, the second upright support member having a second upper portion, a second central portion, and a second lower portion, and wherein the second upright support member comprises at least one resilient stay; and (f) wherein the second upper portion is at a lesser lateral distance from the rear central axis than the second central portion, and wherein the second central portion is at a lesser lateral distance from the rear central axis than the second lower portion; and (g) wherein the second lower portion extends toward the front central axis and adjacent and directly underneath at least a portion of the patella along a front surface of the lower leg, whereby the knee brace provides indirect support to the patella.

10. The knee brace of claim 8 wherein the base is a tubular sleeve.

11. The knee brace of claim 8 wherein the base is an openable and reclosable sleeve.

12. The knee brace of claim 8 wherein the base includes a patella opening.

13. The knee brace of claim 8 wherein the patella opening is roughly circular.

14. A knee brace, comprising:

(a) a base wearable in snug covering relationship to portions of a knee and adjacent portions of an upper leg and a lower leg of a person, the knee having a kneecap and the base having a first lateral side, an upper end, and a lower end;

(b) a first upright support member fastened to the first lateral side, the first upright support member having a first upper portion, a first central portion, and a first lower portion terminating in a first lower end, and wherein the first upright support member comprises at least one resilient stay; and (c) wherein the knee brace has a front central axis when the knee brace is worn, wherein the first upper portion curves away from the front central axis and wherein the first lower portion curves toward the front central axis with the first lower end located adjacent and directly underneath at least a portion of the kneecap along a front surface of the lower leg when the knee brace is worn, whereby the first upright support member is generally shaped like the letter S and whereby the knee brace provides support to the kneecap.

15. The knee brace of claim 14 wherein the base has a second lateral side, and further comprising (d) a second upright support member fastened to the second lateral side, the second upright support member having a second upper portion, a second central portion, and a second lower portion terminating in a second lower end, and wherein the second upright support member comprises at least one resilient stay; and (e) wherein the knee brace has a front central axis when the knee brace is worn, wherein the second upper portion curves away from the front central axis and wherein the second lower portion curves toward the front central axis with the second lower end located adjacent and directly underneath at least a portion of the kneecap along a front surface of the lower leg when the knee brace is worn, whereby the second upright support member is generally shaped like the letter S and whereby the knee brace provides support to the kneecap.

16. The knee brace of claim 14 wherein the base is a tubular sleeve.

17. The knee brace of claim 14 wherein the base is an openable and reclosable sleeve.

18. The knee brace of claim 14 wherein the base includes a patella opening.

19. The knee brace of claim 18 wherein the patella opening is roughly circular.

20. The knee brace of claim 14 wherein the resilient stay includes a flattened spiral core.

* * * * *